United States Patent
Holt et al.

(10) Patent No.: US 6,988,499 B2
(45) Date of Patent: Jan. 24, 2006

(54) MECHANICAL RESUSCITATOR

(75) Inventors: William T. Holt, deceased, late of Bartlett, TN (US); by Leatha J. Holt, legal representative, Bartlett, TN (US)

(73) Assignee: NewAir Manufacturing, LLC, Bartlett, TN (US)

( * ) Notice: Subject to any disclaimer, the term of this patent is extended or adjusted under 35 U.S.C. 154(b) by 334 days.

(21) Appl. No.: 10/105,041

(22) Filed: Mar. 22, 2002

(65) Prior Publication Data

US 2003/0178025 A1 Sep. 25, 2003

(51) Int. Cl.
A62B 16/00 (2006.01)

(52) U.S. Cl. .............................. 128/205.13; 128/205.16; 128/205.17

(58) Field of Classification Search ............. 128/205.13, 128/205.16, 205.17, 205.28, 202.29, 202.16; 601/41, 42, 43, 44
See application file for complete search history.

(56) References Cited

U.S. PATENT DOCUMENTS

| | | |
|---|---|---|
| 1,197,232 A | 9/1916 | Pierpont |
| 1,371,702 A | 3/1921 | Lyon |
| 1,406,141 A | 2/1922 | Anston |
| 2,427,419 A | 9/1947 | Rausch ........................ 128/29 |
| 2,428,451 A | 10/1947 | Emerson ....................... 128/29 |
| 3,461,866 A | 8/1969 | Ritchie ..................... 128/145.7 |
| 3,552,390 A * | 1/1971 | Muller ......................... 601/97 |
| 3,870,038 A * | 3/1975 | Arblaster ..................... 601/41 |
| 4,077,404 A | 3/1978 | Elam ....................... 128/145.8 |
| 4,239,038 A | 12/1980 | Holmes ................. 128/205.13 |
| 4,349,015 A * | 9/1982 | Alferness ..................... 601/41 |
| 4,870,962 A | 10/1989 | Sitnik ..................... 128/205.13 |
| 4,881,540 A * | 11/1989 | Vigilia ................... 128/202.28 |
| 5,009,226 A | 4/1991 | Holt ........................... 128/205 |
| 5,109,833 A * | 5/1992 | Frimberger ................... 601/41 |
| 5,313,938 A * | 5/1994 | Garfield et al. ......... 128/205.16 |
| 5,657,751 A * | 8/1997 | Karr, Jr. ................ 128/205.18 |
| 5,823,185 A * | 10/1998 | Chang ................... 128/204.18 |

* cited by examiner

Primary Examiner—Glenn K. Dawson
Assistant Examiner—Darwin P. Erezo
(74) Attorney, Agent, or Firm—Walker, McKenzie & Walter P.C.

(57) ABSTRACT

An improved resuscitator including a pump, a base member for positioning over the sternum area of the patient's chest, coupling structure for allowing gas to pass from a passageway of the base member to the patient's lungs, and seal structure for forming a gas-tight seal between an opening of the pump and a first end of the passageway of the base member when a bellows-like structure of the pump is moved from a first position to a second position. The improvement includes sternum structure attached to the base member for placement on the patient's chest over the patient's sternum and for applying pressure to the patient's sternum during resuscitation (i.e., when the bellows-like structure of the pump is moved from the first position to the second position).

2 Claims, 2 Drawing Sheets

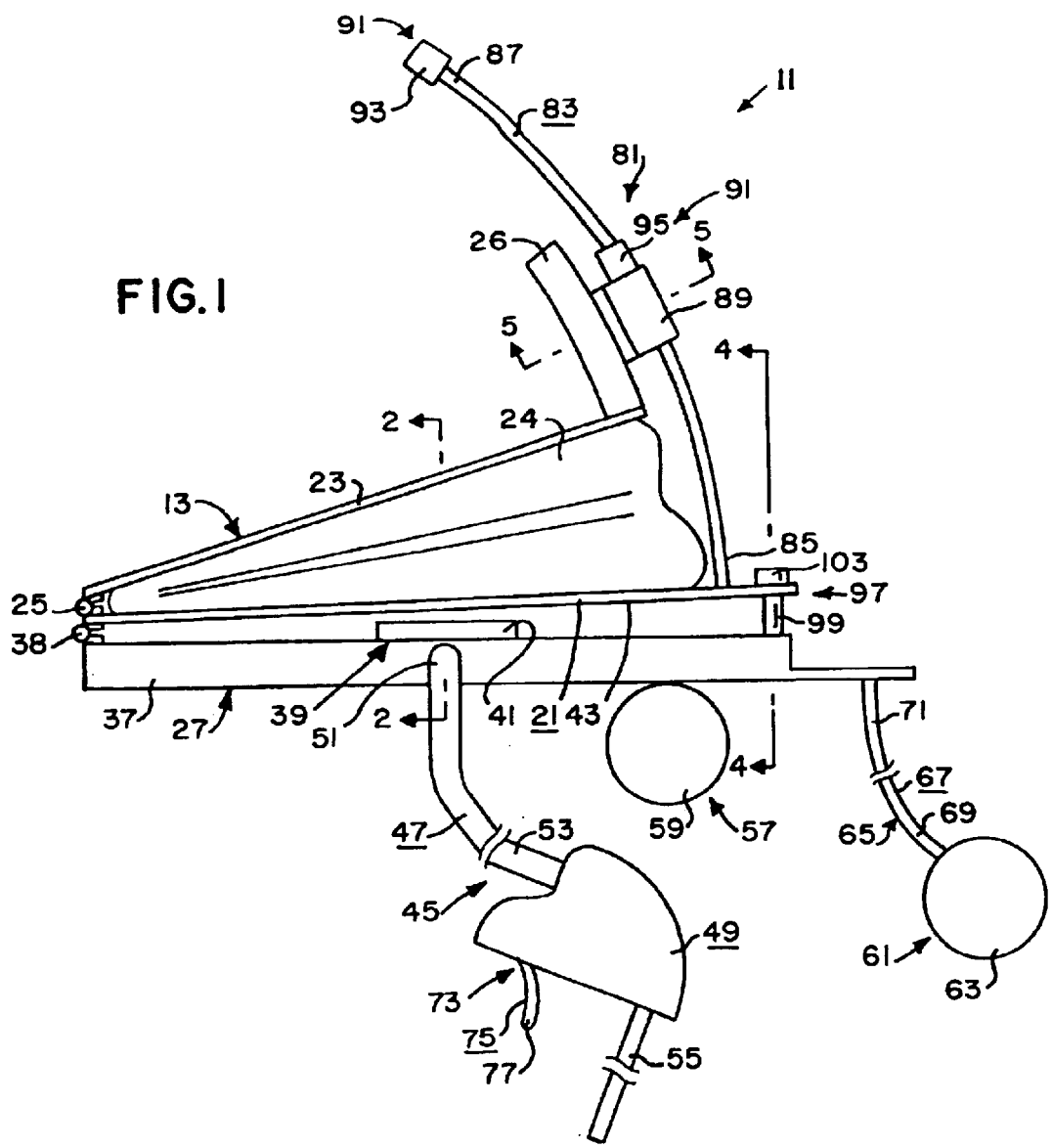
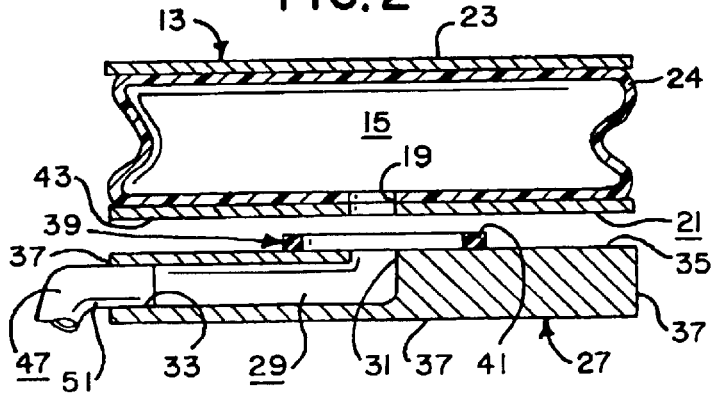

MECHANICAL RESUSCITATOR

BACKGROUND OF THE INVENTION

1. Field of the Invention

The present invention relates, in general, to resuscitators for assisting or reestablishing the breathing of a patient

2. Information Disclosure Statement

The following patents appear to be relevant to the present invention: Pierpont, U.S. Pat. No. 1,197,232, issued July, 1916; Lyon, U.S. Pat. No. 1,371,702, issued March, 1921; Anston, U.S. Pat. No. 1,406,141, issued February, 1922; Rausch, U.S. Pat. No. 2,427,419, issued September, 1947; Emerson, U.S. Pat. No. 2,428,451, issued October, 1947; Ritchie, U.S. Pat. No. 3,461,866, issued August, 1969; Elam, U.S. Pat. No. 4,077,404, issued March, 1978; Holmes, U.S. Pat. No. 4,239,038, issued December, 1980; Sitnik, U.S. Pat. No. 4,870,962, issued October, 1989; and Holt, U.S. Pat. No. 5,009,226, issued Apr. 23, 1991.

Pierpont, U.S. Pat. No. 1,197,232, discloses a device including a hand operated bellows having first and second chambers. When the bellows is operated, positive pressure is created in the first chamber to force oxygen or atmospheric air into a patient's lungs and a vacuum is created in the second chamber to draw vitiated air out of the patient's lungs.

Lyon, U.S. Pat. No. 1,371,702, discloses a device including a hand operated piston coupled to a face mask by first and second conduits. When the piston is operated, positive pressure is created on the downstroke to force air into a patient's lungs and negative pressure is created on the upstroke to draw air from the patient's lungs. Structure is provided to allow the volume of air pumped per pump stroke to be varied.

Anston, U.S. Pat. No. 1,406,141, discloses an apparatus for first drawing impure air out of a patient's body, forcing clean air into the patient's body, and then causing a constant circulation of air for a sufficient time to insure exercise and full expansion of the patient's lungs and bronchial tubes.

Rausch, U.S. Pat. No. 2,427,419, discloses a resuscitating apparatus for forcing gas into a patient's lungs and for exhausting the spent gas from the patient's lungs by suction. The apparatus includes structure for maintaining the positive and negative pressures created thereby within certain limits.

Emerson, U.S. Pat. No. 2,428,451, discloses a pressure resuscitator which intermittently forces air or oxygen into a patient's lungs so as to inflate the lungs, the deflation of the lungs depending upon the elasticity thereof.

Ritchie, U.S. Pat. No. 3,461,866, discloses a respirator including a pair of piston-type pumps connected by a piston rod to a common handle for simultaneous reciprocal operation. One pump is operable on one stroke of the handle to induce inhalation by a patient and the other pump is operable on the other stroke of the handle to induce exhalation by the patient. Valves are provided to prevent excess positive or negative pressures.

Elam, U.S. Pat. No. 4,077,404, discloses a resuscitator valve mechanism having inspiration and expiration ports, and arranged to assure automatic operation to effect oxygen "blow-by" under conditions of operation tending to close the expiration port to thereby prevent undesirable build-up of pressure in the patient's lungs.

Holmes, U.S. Pat. No. 4,239,038, discloses a manually operable resuscitator having a reservoir into which breathable gas is drawn and from which the gas may be directed to a patient, and having a valve assembly which prevents exhaled gas from returning to the reservoir and which keeps the space in which the exhaled gas is retained small to ensure that the subsequent inhalation gases to the patient include only a small proportion of carbon dioxide.

Sitnik, U.S. Pat. No. 4,870,962, discloses a disposable self-inflating manual resuscitator bag that is shaped like a pleated, handleless bellows where the pleats act like a spring following compression to rapidly re-inflate the bag to its fully recovered state.

Holt, U.S. Pat. No. 5,009,226, discloses the present inventor's earlier resuscitator including a pump having a cavity and including movable means movable between a first position and a second position for forcing gas from the cavity of the pump when moved from the first position to the second position and for drawing gas into the cavity of the pump when moved from the second position to the first position, the pump having an opening for allowing gas to be drawn into and forced out of the cavity thereof; a base member having a passageway for allowing gas to pass therethrough, the passageway having a first end and a second end; coupling means for allowing gas to pass from the passageway of the base member to the patient's lungs, the coupling means including a hollow tube for being connected to the second end of the passageway of the base member to allow gas to pass from the passageway of the base member therethrough; and seal means for forming a gas-tight seal between the opening of the pump and the first end of the passageway of the base member when the movable means of the pump is moved from the first position to the second position to allow gas to be forced from the cavity of the pump through the passageway of the base member and out the coupling means.

None of the above patents disclose or suggest the present invention. More specifically, none of the above patents disclose or suggest a resuscitator including a pump having a cavity and including movable means movable between a first position and a second position for forcing gas from the cavity of the pump when moved from the first position to the second position and for drawing gas into the cavity of the pump when moved from the second position to the first position, the pump having an opening for allowing gas to be drawn into and forced out of the cavity thereof; a base member having a passageway for allowing gas to pass therethrough, the passageway having a first end and a second end; coupling means for allowing gas to pass from the passageway of the base member to the patient's lungs, the coupling means including a hollow tube for being connected to the second end of the passageway of the base member to allow gas to pass from the passageway of the base member therethrough; seal means for forming a gas-tight seal between the opening of the pump and the first end of the passageway of the base member when the movable means of the pump is moved from the first position to the second position to allow gas to be forced from the cavity of the pump through the passageway of the base member and out the coupling means; and sternum means attached to the base member for placement on the patient's chest over the patient's sternum and for applying pressure to the patient's sternum during resuscitation.

BRIEF SUMMARY OF THE INVENTION

The present invention is directed toward providing an improved resuscitator for conveying gas to a patient's lungs to assist or re-establish the breathing of the patient. More specifically, the present invention is designed to put unspent air into a patient's lungs, while doing chest impressions or compressions.

The resuscitator of the present invention includes a pump having a cavity and including movable means movable between a first position and a second position for forcing gas from the cavity of the pump when moved from the first position to the second position and for drawing gas into the cavity of the pump when moved from the second position to the first position, the pump having an opening for allowing gas to be drawn into and forced out of the cavity thereof; a base member having a passageway for allowing gas to pass therethrough, the passageway having a first end and a second end; coupling means for allowing gas to pass from the passageway of the base member to the patient's lungs, the coupling means including a hollow tube for being connected to the second end of the passageway of the base member to allow gas to pass from the passageway of the base member therethrough; seal means for forming a gas-tight seal between the opening of the pump and the first end of the passageway of the base member when the movable means of the pump is moved from the first position to the second position to allow gas to be forced from the cavity of the pump through the passageway of the base member and out the coupling means; and sternum means attached to the base member for placement on the patient's chest over the patient's sternum and for applying pressure to the patient's sternum during resuscitation.

One object of the present invention is to provide a resuscitator that can be operated by one person (the "rescuer") to put unspent air into a patient's lungs while doing chest impressions or compressions, with no danger of the rescuer catching a disease from the patient being resuscitated (i.e., without danger of air or fluid from the patient's mouth being forced or expelled into the rescuer's mouth, etc.).

Another object of the present invention is to provide such a resuscitator that will pump unspent air into a patient's mouth and do chest impressions or compressions all in one stroke, while allowing the patient to exhale when a new charge of air is drawn into the resuscitator.

Another object of the present invention is to provide a simple, inexpensive resuscitator designed to save lives without putting the rescuer in danger of catching a disease from the patient.

Another object of the present invention is to provide a simple, inexpensive resuscitator designed to aid in the performance of cardiopulmonary resuscitation (CPR) to save lives without putting the rescuer in danger of catching a disease from the patient.

Another object of the present invention is to provide a resuscitator having a sternum ball that simulates the heal of the hand that is placed on top of the patient's sternum while doing chest compressions during CPR. If there are body fluids on the patient's chest or sternum area, this device will again eliminate the fear associated with CPR because the rescuer's hands are not on the patient's sternum, only the sternum ball.

BRIEF DESCRIPTION OF THE SEVERAL VIEWS OF THE DRAWINGS

FIG. 1 is a side elevational view of a preferred embodiment of the resuscitator of the present invention with portions thereof broken away for clarity.

FIG. 2 is a sectional view substantially as taken on line 2—2 of FIG. 1, on a somewhat enlarged scale and with portions omitted for clarity.

DETAILED DESCRIPTION OF THE INVENTION

The improved resuscitator of the present invention is shown in FIGS. 1–5, and identified by the numeral 11. The resuscitator 11 of the present invention is used to convey gas (e.g., air) to a patient's lungs. More specifically, the resuscitator 11 of the present invention is a manually operated device used to assist or re-establish the breathing of a patient. That is, the resuscitator 11 is used to assist in the performance of cardiopulmonary resuscitation (CPR) and is an improvement over the resuscitator disclosed in the inventor's prior patent, Holt, U.S. Pat. No. 5,009,226, issued Apr. 23, 1991, incorporated herein by reference (see, particularly, column 6, line 1, through column 8, line 57, and FIGS. 5–10 of Holt, U.S. Pat. No. 5,009,226).

Figure 3:
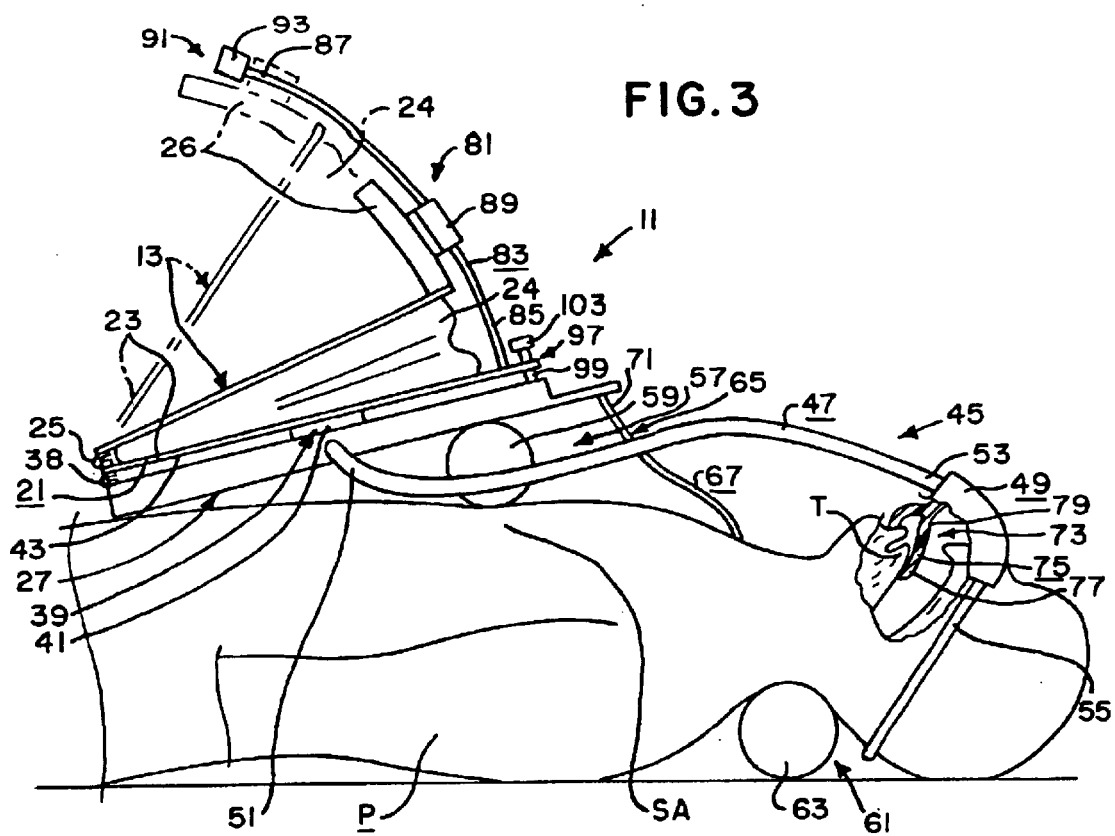
FIG. 3 is a somewhat diagrammatic side elevational view of the resuscitator of FIG. 1, shown in combination with a patient.
Figure 4:
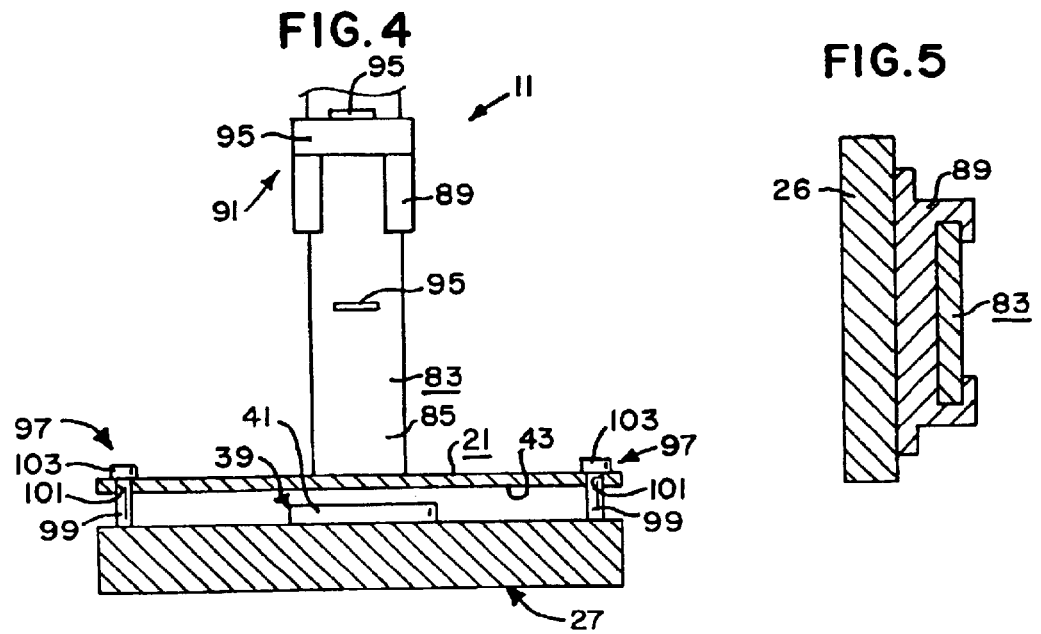
FIG. 4 is a sectional view substantially as taken on line 44 of FIG. 1, on a somewhat enlarged scale and with portions omitted for clarity.
Figure 5:
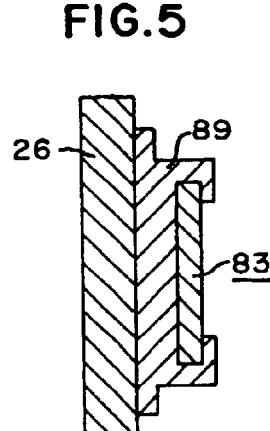
FIG. 5 is a sectional view substantially as taken on line 5—5 of FIG. 1, on a somewhat enlarged scale and with portions omitted for clarity.

The resuscitator 11 includes a pump 13 having a cavity 15, movable means 15 movable between a first or opened position as shown in solid lines in FIG. 1 and in broken lines in FIG. 3, and a second or closed position as shown in solid lines in FIG. 3, for forcing gas (i.e., air) from the cavity 15 of the pump 13 when moved from the first position to the second position and for drawing gas (i.e., air) into the cavity 15 of the pump 13 when moved from the second position to the first position, and an opening 19 for allowing gas to be drawn into and forced out of the cavity 15 therethrough. More specifically, the pump 13 preferably consists of a bellow-like structure having a first or seal plate member 21, a second or movable plate member 23, and an air-impermeable, flexible body member 24 joining the first and second plate members 21, 23 in an accordion-like manner to form a bellows so that gas will be drawn in through the opening 19 into the cavity 15 when the first and second plate members 21, 23 are moved away from one another to the first or opened position, and so that air will be forced out through the opening 19 from the cavity 15 when the first and second plate members 21, 23 are moved toward one another to the second or closed position. A first hinge 25 is preferably provided for hinging one end of the first or seal plate member 21 and one end of the second or movable plate member 23 to one another. The movable means 17 preferably includes a knob or handle 26 attached to the second or movable plate member 23 (preferably to the end of the second or movable plate member 23 opposite the first hinge 25) for being gripped by the user of the resuscitator 11 so that the second or movable plate member 23 can easily be moved between the opened and closed positions, etc., as will now be apparent to those skilled in the art.

The resuscitator 11 includes a base member 27 for positioning over the sternum area SA of the patient's chest. The base member 27 has a passageway 29 for allowing gas to pass therethrough. The passageway 29 has a first end 31 and a second end 33. The base member 27 may consist of a plate-like construct having an upper face 35, a lower face 36, and a side edge 37, with the first end 31 of the passageway 29 located on the upper face 35 and with the second end 31 of the passageway 29 located at the side edge 37. The plate-like construct may consist of a one-piece, integral plate or board like the base member 2.21 shown in Holt, U.S. Pat. No. 5,009,226, or may consist of a multipiece construct having an upper plate, a lower plate, and a plurality of posts or the like joining the upper and lower plates together. A second hinge 38 is preferably provided for hinging one end of the first or seal plate member 21 and one end of the base member 27 to one another.

The resuscitator 11 includes seal means 39 for forming a gas-tight seal between the opening 19 of the pump 13 and the first end 31 of the passageway 29 of the base member 27 when the movable means 17 of the pump 13 is moved from the first or opened position to the second or closed position to allow gas to be forced from the cavity 15 of the pump 13 through the passageway 29 of the base member 27. The seal means 39 preferably consists of a standard rubber O-ring 41 mounted to the upper face 35 of the base member 27 in a position surrounding the first end 31 of the passageway 29 to form a gas-tight seal between the opening 19 of the pump 13 and the first end 31 of the passageway 29 when the movable means 17 of the pump 13 is moved from the first or opened position to the second or closed position. More specifically, the first or seal plate member 21 of the pump 13 has a lower face 43 that is forced against the O-ring 41 of the seal member 39 when the movable means 17 thereof is moved from the first or opened position to the second or closed position to thereby cause the O-ring 41 of the seal member 39 to form a gas-tight seal between the lower face 43 of the first or seal plate member 21 of the pump 13 and the upper face 35 of the base member 27 as will now be apparent to those skilled in the art. The opening 19 of the pump 13 preferably extends through the lower face 43 first or seal plate member 21 and substantially aligns with the first end 31 of the passageway 29 of the base member 27 and is surrounded by the O-ring 41 of the seal member 39 when the movable means 17 of the pump 13 is moved from the first or opened position to the second or closed position, to thereby cause a gas-tight seal to be formed between the opening 19 and the first end 31 of the passageway 29 as will now be apparent to those skilled in the art. When the movable means 17 is moved from the second or closed position to the first or opened position, the seal between the opening 19 and the first end 31 of the passageway 29 will be broken, allowing gas to enter the opening 19 and cavity 15.

The resuscitator 11 includes coupling means 45 for allowing gas to pass from the passageway 29 of the base member 27 to the patient's lungs. The coupling means 45 includes a hollow tube 47 connected to the second end 33 of the passageway 29 of the base member 27 to allow gas to pass from the cavity 15 of the pump 13 through the hollow tube 47. The coupling means 45 preferably includes a face mask 49 for being positioned over the patient's mouth and nose, etc., as will now be apparent to those skilled in the art, and the hollow tube 47 preferably has a first end 51 for being connected to the second end 33 of the passageway 29 of the base member 27, and a second end 53 for forming or being coupled to the face mask 49 to allow gas to pass from the cavity 15 of the pump 13 through the hollow tube 47 and face mask 49 into the patient's mouth, etc., as will now be apparent to those skilled in the art. An elastic band 55 may be attached to the face mask 49 for extending around the back of the patient's head to hold the face mask 49 securely over the patient's mouth and nose, etc.

The improvement of the present invention includes sternum means 57 attached to the base member 27 for placement on the patient's chest over the patient's sternum or sternum area SA and for applying pressure to the patient's sternum or sternum area SA during resuscitation. More specifically, the sternum means 57 preferably consists of a ball-like member 59 fixedly secured to the lower face 36 of the base member 27 in a position so that when the base member 27 is positioned over the sternum area SA of the patient's chest, the ball-like member 59 of the sternum means 57 will be placed on the patient's chest over the patient's sternum or sternum area SA.

The improvement of the present invention preferably includes neck positioning means 61 for maintaining the patient's airway open during resuscitation. The neck positioning means 61 may consist of a firm pillow-like member 63 secured to the base member 27 by string means 65 for placement under the patient's neck during resuscitation to support the patient's neck and properly limit head and neck movement during resuscitation and keep the patient's head properly tilted and airway open during forced air compressions and force chest compression. The string means 65 may consist of an elastic band 67 having a first end 69 attached to the pillow-like member 63 and a second end 71 attached to the base member 27. The neck positioning means 61 is very important because it keeps the patient's head tilted at all times. This will allow the patient's airway to remain open at all times. If the patient's airway is not open while pumping unspent air into the patient's mouth, the unspent air will not enter or exit the patient's lungs.

The improvement of the present invention preferably includes tongue holding means 73 for preventing the patient's tongue T from being swallowed during resuscitation. The tongue holding means 73 preferably includes an elongated finger-like member 75 having a first end 77 for inserting into the patient's mouth over the patient's tongue T, and having a second end 79 attached to the face mask 49.

The improvement of the present invention preferably includes an improved control means 81 for controlling the amount of gas forced from the cavity 15 of the pump 13 when the movable means 17 is moved from the first or opened position to the second or closed position.

The improved control means 81 preferably includes an elongated post or leg member 83 having a first end 85 attached to the base member 27, and a second end 87. The improved control means 81 further includes a follower member 89 attached to the second or movable plate member 23 of the pump 13 and engaging the post member 83 in a manner to slide up and down on the post member 83. The post member 83 is preferably curved based on a radius extending from the pivot point of the first hinge 25 so that as the follow member 89 slides up and down the post member 83, the second or movable plate member 23 will pivot up and down about the first hinge 25 as will now be apparent to those skilled in the art.

The improved control means 81 preferably includes limit means 91 for limiting the travel of the second or movable plate member 23, to thereby control or regulate the amount of gas pumped by the resuscitator 11 during a single stroke (i.e., during one movement of the second or movable plate member 23 between the opened and closed positions). The limit means 91 may include a fixed stop member 93 attached to the upper or distal end of the post member 83 and for being engaged by a portion of the follower member 89 when the second or movable plate member 23 is raised to opened position to thereby limit the travel of the second or movable plate member 23 to that maximum point and thereby limit the effective maximum volume of the cavity 15 and the maximum amount of gas that can be forced from the cavity 15 when the movable means 17 is moved between the first or opened position and the second or closed position. In addition, the limit means 91 preferably includes a movable stop member 94 attached to the post member 83 in a manner that allows the movable stop member 94 to be moved up and down on the post member 83 (or removed completely from the post member 83) to allow adjustment of the limit of travel of the second or movable plate member 23 and, thus, allow the amount of gas that is forced from the cavity 15 when the movable means 17 is moved from the first or opened position to the second or closed position to be likewise varied as will now be apparent to those skilled in the art. The movable stop member 94 may be movably attached to the post member 83 in any common manner such as by thumb screws, pegs, or the like (not shown) to allow the user of the resuscitator 11 to easily and quickly adjust the maximum travel of the plate member 23, and thus the amount of gas pumped by a single stroke of the resuscitator 11, etc., as will now be apparent to those skilled in the art. The post member 83 may be labeled, via marking or indicia 95 (see FIG. 4), to defined the maximum suggested movement or travel of the plate member 23 (and thus the volume of gas pumped per single stroke of the resuscitator 11) for different type patients (e.g., adult or child), so that the user of the resuscitator 11 can either use the markings to gauge the travel of the movable means 17 or set the movable stop member 94 to the desired or appropriate indicia 95 so that the stop member 94 will provide a positive limit on the travel of the movable second or movable plate member 23, etc.

The improvement of the present invention may also include check means 97 for checking, or limiting, pivotal movement of the first or seal plate member 21 from the base member 27. The check means 97 may consist simply of one or more posts 99 extending from the upper face 37 of the base member 27 up through corresponding apertures 101 in the first or seal plate member 21 on the end of the base member 27 and first or seal plate member 21 opposite the hinge 38, with each post 99 having an enlarged head 103 at the distal end thereof larger than the corresponding aperture 101 to thereby stop the first or seal plate member 21 from pivoting more than a certain amount (defined by the height of the posts 99) away from the base member 27 when the movable means 17 is moved from the second or closed position to the first or opened position.

To use the preferred embodiment of the resuscitator of the present invention, the patient P is typically placed supine on a support surface (e.g., the ground), the pillow-like member 63 of the neck positioning means 61 is placed under the patient's neck to limit head and neck movement during CPR and to keep the patient's head tilted and the patient's airway open during forced air compressions and forced chest compressions, and the face mask 49 is placed over the patient's mouth with the finger-like member 75 of the tongue holding means 73 extending over the patient's tongue T to help prevent the patient P from swallowing his/her tongue T during CPR, etc. In order to do chest impressions or compressions with the resuscitator 11 at the same time gas is being pumped into the patient's lungs, the base member 27 of the resuscitator 11 is placed on the patient's chest with the ball-like member 59 of the sternum means 57 over the patient's sternum area SA. The pump 13 can then be activated to convey gas to the patient's lungs. That is, the rescuer can then grab the handle 26 and lift the second or movable plate member 23 from the closed to the opened position (as limited by either the fixed or movable stop member 93, 94 of the limit means 91), causing the first or seal plate member 21 to lift away from the base member 27 (as limited by the check means 97) and breaking any seal formed by the seal means 39, and causing gas (air) to be drawn into the cavity 15 of the pump 13 through the opening 19. Next, the rescuer uses the handle 26 to force the second or movable plate member 23 from the opened position to the closed position in a single stroke, causing the first or seal plate member 21 to pivot toward the upper face 35 of the base member 27, causing the seal means 39 to form a gas-tight seal between the opening 19 of the pump 13 and the first end 31 of the passageway 29 of the base member 27 and causing gas to be forced from the cavity 15 of the pump 13 through the opening 19, through the passageway 29, through the hollow tube 47 and into the patient's airway and lungs. Simultaneously, while forcing the second or movable plate member 23 from the opened position to the closed position in a single stroke, the ball-like member 59 of the sternum means 57 will be forced against the patient's sternum area SA, effecting a chest compression of the patient's chest and enhancing the resuscitation effort as will now be apparent to those skilled in the art. The rescuer will then repeat the process by lifting the second or movable plate member 23 from the closed to the opened position, causing the first or seal plate member 21 to lift away from the base member 27 and breaking the seal between the opening 19 and passageway 29 so that the patient can exhale as will now be apparent to those skilled in the art. The up and down movement of the second or movable plate member 23 will be transferred to the patient's chest, thereby enhancing the resuscitation effort.

Although the present invention has been described and illustrated with respect to a preferred embodiment and a preferred use therefor, it is not to be so limited since modifications and changes can be made therein which are within the full intended scope of the invention.

What is claimed is:

1. An improved resuscitator including
   a pump including movable means movable between a first position and a second position for forcing gas from the pump when moved from the first position to the second position and for drawing gas into the pump when moved from the second position to the first position, the pump having an opening for allowing gas to be drawn into and forced out therethrough;
   a base member for positioning over the sternum area of the patient's chest, the base member having a passageway for allowing gas to pass therethrough, the passageway having a first end and a second end;
   coupling means for allowing gas to pass from the passageway of the base member to the patient's lungs, the coupling means including a hollow tube for being connected to the second end of the passageway of the base member to allow gas to pass from the passageway of the base member therethrough; and
   seal means for forming a gas-tight seal between the opening of the pump and the first end of the passageway of the base member when the movable means of the pump is moved from the first position to the second position to allow gas to be forced from the pump through the passageway of the base member and out the coupling means;
   wherein the improvement comprises:
   sternum means attached to the base member for placement on the patient's chest over the patient's sternum and for applying pressure to the patient's sternum during resuscitation; said sternum means consisting of a ball-like member for simulating the heel of a person's hand when applying pressure to the patient's sternum while performing cardiopulmonary resuscitation.

2. The improved resuscitator of claim 1 wherein the improvement further includes: neck positioning means for maintaining the patient's airway open during resuscitation.

* * * * *

UNITED STATES PATENT AND TRADEMARK OFFICE
CERTIFICATE OF CORRECTION

PATENT NO. : 6,988,499 B2  Page 1 of 1
APPLICATION NO. : 10/105041
DATED : January 24, 2006
INVENTOR(S) : William T. Holt, deceased, Leatha J. Holt, legal representative and Darrell K. Thompson It is certified that error appears in the above-identified patent and that said Letters Patent is hereby corrected as shown below:

<u>Title page,</u>
Item [75], Inventors, change
"Willaim T. Holt, deceased, late of Bartlett, TN (US); by Leatha J. Holt, legal representative, Bartlett, TN (US)" to
-- William T. Holt, deceased, late of Bartlett, TN (US); by Leatha J. Holt, legal representative, Bartlett, TN (US); and Darrell K. Thompson, Memphis, TN (US) --.

Signed and Sealed this

Twenty-seventh Day of June, 2006

JON W. DUDAS
*Director of the United States Patent and Trademark Office*